United States Patent
Magnuson

(10) Patent No.: US 6,201,170 B1
(45) Date of Patent: Mar. 13, 2001

(54) GARDEN BEAN NAMED 206999

(75) Inventor: D. Stephen Magnuson, Gilroy, CA (US)

(73) Assignee: Harris Moran Seed Company, Modesto, CA (US)

(*) Notice: Subject to any disclaimer, the term of this patent is extended or adjusted under 35 U.S.C. 154(b) by 0 days.

(21) Appl. No.: 09/410,611

(22) Filed: Oct. 1, 1999

(51) Int. Cl.$^7$ ............... A01H 5/00; A01H 5/10; A01H 4/00; A01H 1/00; C12N 5/04

(52) U.S. Cl. ............ 800/313; 800/298; 800/260; 800/265; 435/410; 435/430; 435/430.1

(58) Field of Search ................... 800/260, 265, 800/268, 298, 313; 435/410, 430, 430.1

(56) References Cited

U.S. PATENT DOCUMENTS 4,769,512 * 9/1988 Schulbach ................ 800/1

OTHER PUBLICATIONS

Plant Variety Protection Certificate for Bean "Quest".

* cited by examiner

*Primary Examiner*—Gary Benzion
*Assistant Examiner*—Melissa L. Kimball
(74) *Attorney, Agent, or Firm*—Rothwell, Figg, Ernst & Manbeck

(57) ABSTRACT

A novel garden bean cultivar, designated '206999', is disclosed. The invention relates to the seeds of garden bean cultivar '206999', to the plants of garden bean '206999' and to methods for producing a garden bean plant produced by crossing the cultivar '206999' with itself or another garden bean variety. The invention further relates to hybrid garden bean seeds and plants produced by crossing the cultivar '206999' with another garden bean cultivar.

13 Claims, No Drawings

GARDEN BEAN NAMED 206999

BACKGROUND OF THE INVENTION

The present invention relates to a new and distinctive garden bean (*Phaseolus vulgaris* L.) variety, designated '206999'. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior garden bean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same garden bean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new garden bean cultivars.

The development of new garden bean cultivars requires the development and selection of garden bean varieties, the crossing of these varieties and selection of superior hybrid crosses. The hybrid seed is produced by manual crosses between selected male-fertile parents. These hybrids are selected for certain genetic traits such as pod straightness, erect habit, root structure and disease resistance. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Garden bean, *Phaseolus vulgaris*, is an important and valuable vegetable crop. Thus, a continuing goal of plant breeders is to develop stable, high yielding garden bean cultivars that are agronomically sound. The reasons for this goal are obviously to maximize the amount of yield produced on the land. To accomplish this goal, the garden bean breeder must select and develop garden bean plants that have the traits that result in superior cultivars.

SUMMARY OF THE INVENTION

According to the invention, there is provided a novel garden bean cultivar, designated '206999'. This invention thus relates to the seeds of garden bean cultivar '206999', to the plants of garden bean '206999' and to methods for producing a garden bean plant produced by crossing the garden bean '206999' with itself or another garden bean line.

Thus, any such methods using the garden bean variety '206999' are part of this invention: selfing, backcrosses, hybrid production, crosses to populations, and the like. All plants produced using garden bean variety '206999' as a parent are within the scope of this invention. Advantageously, the garden bean variety could be used in crosses with other, different, garden bean plants to produce first generation ($F_1$) garden bean hybrid seeds and plants with superior characteristics.

In another aspect, the present invention provides for single gene converted plants of '206999'. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring garden bean gene or a transgene introduced through genetic engineering techniques.

In another aspect, the present invention provides regenerable cells for use in tissue culture of garden bean plant '206999'. The tissue culture will preferably be capable of regenerating plants having the physiological and morphological characteristics of the foregoing garden bean plant, and of regenerating plants having substantially the same genotype as the foregoing garden bean plant. Preferably, the regenerable cells in such tissue cultures will be embryos, seeds and meristematic cells. Still further, the present invention provides garden bean plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Maturity Date

Plants are considered mature when the pods have reached their maximum allowable seed size and sieve size for the specific use intended. This can vary for each end user, e.g., processing at different stages of maturity would be required for different types of consumer beans such as "whole pack," "cut" or "french style". The number of days are calculated from a relative planting date which depends on day length, heat units and environmental other factors.

Sieve Size (sv)

Sieve size 1 means pods which fall through a sieve grader which culls out pod diameters of 4.76 cm through 5.76 cm. Sieve size 2 means pods which fall through a sieve grader which culls out pod diameters of 5.76 cm through 7.34 cm. Sieve size 3 means pods which fall through a sieve grader which culls out pod diameters of 7.34 cm through 8.34 cm. Sieve size 4 means pods which fall through a sieve grader which culls out pod diameters of 8.34 cm through 9.53 cm. Sieve size 5 means pods which fall through a sieve grader which culls out pod diameters of 9.53 cm through 10.72 cm. Sieve size 6 means pods which fall through a sieve grader which culls out pod diameters of 10.72 cm or larger.

Bean Yield (Tons/Acre)

The yield in tons/acre is the actual yield of the beans at harvest.

Plant Height

Plant height is taken from the top of soil to top node of the plant and is measured in centimeters.

Allele

Allele is any of one or more alternative forms of a gene, all of which alleles relate to one trait or characteristic. In a diploid cell or organism, the two alleles of a given gene occupy corresponding loci on a pair of homologous chromosomes.

Backcrossing

Backcrossing is a process in which a breeder repeatedly crosses hybrid progeny back to one of the parents, for example, a first generation hybrid $F_1$ with one of the parental genotypes of the $F_1$ hybrid.

Quantitative Trait Loci (QTL)

Quantitative trait loci (QTL) refer to genetic loci that control to some degree numerically representable traits that are usually continuously distributed.

Regeneration

Regeneration refers to the development of a plant from tissue culture.

DETAILED DESCRIPTION OF THE INVENTION

Garden bean cultivar '206999' has superior characteristics and was developed from the cross of 'Quest'×HM5991. The F$_1$ plants were grown in a greenhouse during the Spring of 1992. F$_2$ selection was made at the San Juan Bautista Research Station in the Fall of 1992. The F$_3$ selections were made in the Summer of 1993 at San Juan Bautista; F$_4$ plants were selected in Wisconsin; F$_5$ selections were made in February, 1995 at Los Mochis, Mexico; F$_6$ selections were made in Summer, 1995 in Wisconsin and one selection was bulked in February, 1996 in Mexico for observation.

Some of the criteria used to select in various generations include: pod appearance, bean yield, pod set height, emergence, disease tolerance, maturity, and plant height.

The cultivar has shown uniformity and stability, as described in the following variety description information. It has been self-pollinated a sufficient number of generations with careful attention to uniformity of plant type. The line has been increased with continued observation for uniformity.

Garden bean cultivar '206999' has the following morphologic and other characteristics (based primarily on data collected at San Juan Bautista).

VARIETY DESCRIPTION INFORMATION

1. MARKET MATURITY
Days to edible pods: 60 days
Number of days earlier than HM5991: 5 days
2. PLANT
Spacing between plants in a row: 8.5 cm
Habit: Determinate
Height: 18 cm
   Shorter than Tendercrop by 2 cm
   Same height as Bush Blue Lake 290
Spread: 23 cm
   Narrower than Tendercrop by 2 cm
Pod Position: High
Bush form: High
3. LEAVES
Surface: Intermediate
Size: Medium
Color: Dark green
4. ANTHOCYANIN PIGMENT
Flowers: Absent
Stems: Absent
Pods: Absent
Seeds: Absent
Leaves: Absent
Petioles: Absent
Peduncles: Absent
Nodes: Absent
5. FLOWER COLOR
Color of standard: White
Color of wings: White
Color of keel: White
6. PODS (edible maturity)
Exterior color: Dark green
Processed pods: Dark green
Dry pod color: Buckskin
Pod Shape: 2.5—[Heart(Pear)=2; Round=3]
Creaseback: Absent
Pubescence: None
Construction: None
Spur length: 7 mm
Fiber: None
Number seeds/pod: 6
Suture string: Absent
Seed development: Slow
Machine harvest: Adapted
Distribution of sieve size at optimum maturity:
   3% 4.76–5.76 cm—Sieve 1
   17% 5.76–7.34 cm—Sieve 2
   57% 7.34–8.34 cm—Sieve 3
   23% 8.34–9.53 cm—Sieve 4
Average Length of 3 sieve: 13.5 cm
Average Length of 4 sieve: 14.5 cm
7. SEED COLOR
Seed coat luster: Semi-shiny
Seed coat: Monochrome
Primary color: White
Hilar ring: Absent
8. SEED SHAPE AND SIZE
Hilum view: Elliptical
Cross section: Oval
Side view: Oval to oblong
Seed size: 24 gm/100 seeds
Lighter than Goldrush by 2.8 gm/100 seeds
9. DISEASE RESISTANCE
Anthracnose (*Colletotrichum lindemuthianum*)
   Race Delta: Resistant
   Race Lambda: Resistant
Bean Rust (*Uromyces appendiculatus*)
   Race 38: Susceptible
Fusarium Root Rot (*Fusarium solanif.* sp. *phaseoli*):
   Moderately Tolerant
Aphanomyces Root Rot (*Aphanomyces euteiches*): Susceptible
Bacterial Brown Spot (*Pseudomonas syringae* pv. *syringae*): Intermediate
Halo Blight (*Pseudomanas syringae* pv. *phaseolicola*):
   Race 2 Susceptible
Bean Common Mosaic Virus (BCMV)
   NY15 Resistant
   NL3 Susceptible
Curly Top Virus (BCTV): Resistant
Calico Mosaic Virus (Western Mexico strain of Golden Mosaic): Highly Tolerant This invention is also directed to methods for producing a garden bean plant by crossing a first parent garden bean plant with a second parent garden bean plant, wherein the first or second garden bean plant is the garden bean plant from the line '206999'. Further, both first and second parent garden bean plants may be from the cultivar '206999'. Therefore, any methods using the cultivar '206999' are part of this invention: selfing, backcrosses, hybrid breeding, and crosses to populations. Any plants produced using cultivar '206999' as a parent are within the scope of this invention.

As used herein, the term "plant" includes plant cells, plant protoplasts, plant cells of tissue culture from which garden bean plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells which upon growth and differentiation produce a cultivar having essentially all of the physiological and morphological characteristics of '206999'.

Culture for expressing desired structural genes and cultured cells are known in the art. Also as known in the art, garden beans are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of Agrobacterium vectors systems and methods for Agrobacterium-mediated gene transfer provided by Gruber, et al., supra.

Procedures for garden bean transformation have been described by: McClean, P., et al. (1991): "Susceptibility of Dry Bean (*Phaseolus-Vulgaris L.*) to Agrobacterium Infection—Transformation of Cotyledonary and Hypocotyl Tissues." *Plant Cell Tissue Org. Cult.* 24(2, February), 131–138. Russell, D. R., et al. (1993): "Stable Transformation of *Phaseolus vulgaris* via Electric-Discharge Mediated Particle Acceleration." *Pl. Cell. Rep.* 12(3, January), 165–169. Franklin, C.I., et al. (1993): "Genetic Transformation of Green Bean Callus via Agrobacterium Mediated DNA Transfer." *Pl. Cell. Rep.* 12(2, January), 74–79. Aragao, F. J. L., et al. (1992): "Particle Bombardment-Mediated Transient Expression of a Brazil Nut Methionine-Rich Albumin in Bean (*Phaseolus vulgaris L.*)." *Plant Mol. Biol.* 20(2, October), 357–359. Aragao, F. J. L., et al. (1993): "Factors Influencing Transient Gene Expression in Bean (*Phaseolus vulgaris L.*) Using an Electrical Particle Acceleration Device " *Pl. Cell. Rep.* 12(9, July), 483–490. Francisco Aragao (1996): "Inheritance of foreign genes in transgenic bean (*Phaseolus vulgaris L.*) co-transformed via particle bombardment." *Theor. Appl. Genet.* 93: 142–150. Zhang, Z., et al. (1997): "Factors Affecting Agrobacterium-mediated Transformation of Common Bean." *J. Amer. Soc. Hort. Sci.* 122(3): 300–305.Kim, J.; Minamikawa, T. (1996): "Transformation and regeneration of French bean plants by the particle bombardment process." *Plant Science* 117: 131–138. Saker, M.; Kuhne, T. (1997/98): "Production of transgenic kidney bean shoots by electroporation of intact cells." *Biologia Plantarum* 40(4): 507–514.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

The present invention contemplates a garden bean plant regenerated from a tissue culture of a variety (e.g., '206999') or hybrid plant of the present invention. As is well known in the art, tissue culture of garden bean can be used for the in vitro regeneration of a garden bean plant. Tissue culture of various tissues of garden beans and regeneration of plants therefrom is well known and widely published. For example, reference may be had to McClean, P.; Grafton, K. F. (1989): "Regeneration of dry bean (*Phaseolus vulgaris*) via organogenesis." *Plant Sci.* 60, 117–122. Mergeai, G.; Baudoin, J. P. (1990): "Development of an in vitro culture method for heart-shaped embryo in *Phaseolus vulgaris.*" B.I.C. Invit. Papers 33, 115–116. Vanderwesthuizen, A. J.; Groenewald, E. G. (1990): "Root Formation and Attempts to Establish Morphogenesis in Callus Tissues of Beans (*Phaseolus-Vulgaris L.*)." *S. Afr. J. Bot.* 56(2, April), 271–273. Benedicic, D., et al. (1990): "The regeneration of *Phaseolus vulgaris* plants from meristem culture." Abst. 5th I.A.P.T.C. Cong. 1, 91 (#A3-33). Genga, A.; Allavena, A. (1990): "Factors affecting morphogenesis from immature cotyledons of *Phaseolus coccineus L.*" Abst. 5th I.A.P.T.C. Cong. 1, 101 (#A3-75). Vaquero, F., et al. (1990): "Plant regeneration and preliminary studies on transformation of *Phaseolus coccineus.*" Abst. 5th I.A.P.T.C. Cong. 1, 106 (#A3-93). Franklin, C. I., et al. 1991): "Plant Regeneration from Seedling Explants of Green Bean (*Phaseolus-Vulgaris L.*) via Organogenesis." *Plant Cell Tissue Org. Cult.* 24 (3, March), 199–206. Malik, K. A.; Saxena, P. K. (1991): "Regeneration in *Phaseolus-Vulgaris L.*—Promotive Role of N6-Benzylaminopurine in Cultures from Juvenile Leaves." *Planta* 184(1), 148–150. Genga, A.; Allavena, A. (1991): "Factors affecting morphogenesis from immature cotyledones of *Phaseolus coccineus L.*" *Plant Cell Tissue Org. Cult.* 27, 189–196. Malik, K. A.; Saxena, P. K. (1992): "Regeneration in *Phaseolus vulgaris L.* —High-Frequency Induction of Direct Shoot Formation in Intact Seedings by N-6-Benzylaminopurine and Thidiazuron." 186 (3, February), 384–389. Malik, K. A.; Saxena, P. K. (1992): "Somatic Embryogenesis and Shoot Regeneration from Intact Seedlings of *Phaseolus acutifolius A., P. aureus (L.)* Wilczek, *P. coccineus L.,* and *P. wrightii L.*" *Pl. Cell. Rep.* 11(3, April), 163–168. Chavez, J., et al. (1992): "Development of an in vitro culture method for heart shaped embryo in *Phaseolus polyanthus.*" B.I.C. Invit. Papers 35, 215–216. Munoz-Florez, L. C., et al. (1992): "Finding out an efficient technique for inducing callus from Phaseolus microspores." B.I.C. Invit. Papers 35, 217–218. Vaquero, F., et al. (1993): "A Method for Long-Term Micropropagation of *Phaseolus coccineus L.*" *L. Pl. Cell. Rep.* 12 (7–8, May), 395–398. Lewis, M. E.; Bliss, F. A. (1994): "Tumor Formation and beta-Glucuronidase Expression in *Phaseolus Vulgaris* Inoculated with *Agrobacterium Tumefaciens.*" *Journal of the American Society for Horticultural Science* 119 (2, March), 361–366. Song, J. Y., et al. (1995): "Effect of auxin on expression of the isopentenyl transferase gene (ipt) in transformed bean (*Phaseolus vulgaris L.*) single-cell clones induced by *Agrobacterium tumefaciens* C58." *J. Plant Physiol.* 146 (1–2, May), 148–154. Thus, another aspect of this invention is to provide cells which upon growth and differentiation produce garden bean plants having the physiological and morphological characteristics of variety '206999'.

The cultivar '206999' has very dark, attractive, glossy pods, with a high pod set height, which are on an erect machine harvestable bush. '206999' is tolerant to Bacterial Brown Spot, resistant to Curly Top Virus and highly tolerant to the Calico Mosaic Virus of western Mexico.

The cultivar '206999' is similar to 'HM5991'. While similar to 'HM5991', there are numerous differences including: '206999' has an average length of approximately 13.5 and 14.5 cm for the 3 and 4 sieve pods, respectively, while HM5991 only measures 10.4 and 11.3 cm, respectively. 206999 is Curly Top Virus resistant and anthracnose (Co-2 gene) resistant whereas HM5991 is not.

TABLES

In Tables 1 and 2 that follow, the percentage of bean pod with different sieve sizes is shown. The first column lists the variety tested. The second column shows the harvest date. Columns 3–6 show the percentage of beans for different sieve sizes 3, 4, 5 and 6 respectively. Column 7 lists the yield in tons per acre.

TABLE 1

1998 Oregon Bean Trial #1

| Variety | Harvest Date | % 1–3 sv | % 4 sv | % 5 sv | % 6 sv | Yield T/Acre |
|---|---|---|---|---|---|---|
| Medinah | Jul. 17 | 100 | 0 | 0 | 0 | 4.36 |
| Shade | Jul. 14 | 68 | 29 | 3 | 0 | 2.35 |
| Hystyle | Jul. 15 | 33 | 36 | 23 | 8 | 4.75 |
| 206999 | Jul. 16 | 78 | 22 | 0 | 0 | 5.02 |
| HMX5991 | Jul. 17 | 92 | 8 | 0 | 0 | 3.91 |
| FM683 | Jul. 16 | 48 | 33 | 19 | 0 | 3.14 |
| FM658 | Jul. 15 | 25 | 49 | 22 | 4 | 3.52 |
| FM549 | Jul. 14 | 33 | 41 | 20 | 6 | 3.21 |
| XPB376 | Jul. 15 | 49 | 37 | 14 | 0 | 3.19 |
| 5402 | Jul. 16 | 65 | 35 | 0 | 0 | 4.01 |

TABLE 2

1998 Oregon Bean Trial #2

| Variety | Harvest Date | % 1–3 sv | % 4 sv | % 5 sv | % 6 sv | Yield T/Acre |
|---|---|---|---|---|---|---|
| Hystyle | Jul. 29 | 36 | 47 | 15 | 2 | 5.96 |
| 206999 | Jul. 29 | 87 | 13 | 0 | 0 | 5.86 |
| HMX5991 | Jul. 31 | 92 | 8 | 0 | 0 | 5.72 |
| FM683 | Jul. 29 | 39 | 34 | 25 | 2 | 6.13 |
| FM658 | Jul. 29 | 22 | 54 | 24 | 0 | 6.45 |
| FM549 | Jul. 29 | 27 | 57 | 16 | 0 | 7.99 |
| 91-G | Jul. 28 | 27 | 49 | 21 | 3 | 5.72 |

DEPOSIT INFORMATION

A deposit of the Harris Moran Seed Company garden bean 206999 disclosed above and recited in the appended claims has been made with the American Type Culture Collection (ATCC), 10801 University Boulevard, Manassas, Va. 20110. The date of deposit was Nov. 29, 2000. The deposit of 2,500 seeds were taken from the same deposit maintained by Harris Moran Seed Company since prior to the filing date of this application. All restrictions upon the deposit have been removed, and the deposit is intended to meet all of the requirements of 37 C.F.R. §1.801–1.809. The ATCC accession number is PTA-2735. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A *Phaseolus vulgaris* garden bean seed designated '206999', wherein a sample of said seed has been deposited under ATCC Accession No. PTA-2735.

2. A plant, or its parts, produced by growing the seed of claim 1.

3. Pollen of the plant of claim 2.

4. An ovule of the plant of claim 2.

5. A *Phaseolus vulgaris* garden bean plant having all of the physiological and morphological characteristics of the garden bean plant of claim 2, or its parts.

6. Tissue culture of the seed of claim 1.

7. A *Phaseolus vulgaris* garden bean plant regenerated from the tissue culture of claim 6, capable of expressing all the morphological and physiological characteristics of *Phaseolus vulgaris* garden bean plant '206999' representative seeds of said plant having been deposited under ATCC No. PTA-2735.

8. Tissue culture of regenerable cells of the plant, or its parts, of claim 2.

9. The tissue culture of claim 8 selected from the group consisting of protoplasts and calli, wherein the regenerable cells are derived from embryos, meristematic cells, pollen, leaves, anthers, roots, root tips, flowers, seeds, stems, or pods.

10. A *Phaseolus vulgaris* garden bean plant regenerated from the tissue culture of claim 9, capable of expressing all the morphological and physiological characteristics of *Phaseolus vulgaris* garden bean plant '206999' representative seeds of said plant having been deposited under ATCC No. PTA-2735.

11. A method for producing a garden bean seed comprising crossing a first parent garden bean plant with a second parent garden bean plant and harvesting the resultant hybrid garden bean seed, wherein said first or second parent garden bean plant is the *Phaseolus vulgaris* garden bean plant of claim 2.

12. A hybrid garden bean seed produced by the method of claim 11.

13. A hybrid garden bean plant, or its parts, produced by growing said hybrid garden bean seed of claim 12.

* * * * *